United States Patent [19]

Mihailovski et al.

[11] 4,045,471
[45] Aug. 30, 1977

[54] PROCESS FOR PREPARING N-CARBAMOYL ETHYL OXANILATES

[75] Inventors: Alexander Mihailovski, Kensington; Jimmy H. Chan, Martinez, both of Calif.

[73] Assignee: Stauffer Chemical Company, Westport, Conn.

[21] Appl. No.: 582,054

[22] Filed: May 29, 1975

[51] Int. Cl.² .................. C07C 127/22; C07C 131/11; C07D 207/06; C07D 295/20
[52] U.S. Cl. ......................... 260/471 A; 260/293.77; 260/326.4; 544/165
[58] Field of Search .............. 260/471 A, 247.2 A, 260/293.77, 326.4

[56] References Cited

U.S. PATENT DOCUMENTS

| 3,210,369 | 10/1965 | Smith et al. ............... 260/471 A X |
| 3,318,842 | 5/1967 | Blachere et al. ............ 260/471 A X |
| 3,843,716 | 10/1974 | Luethi et al. .................. 260/471 A |

*Primary Examiner*—Richard L. Raymond
*Attorney, Agent, or Firm*—Joel G. Ackerman

[57] ABSTRACT

N-carbamoyl ethyl oxanilates having the formula

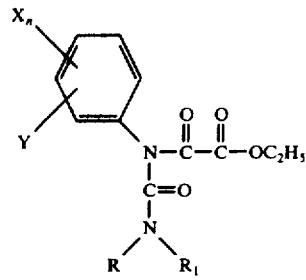

wherein X and Y are independently selected from the group consisting of chloro, bromo and trifluoromethyl; $n$ is either zero or one; and R and $R_1$ are independently selected from the group consisting of lower alkyl and lower alkoxy from $C_1$ to $C_3$ inclusive, or R and $R_1$ taken together is selected from the group consisting of

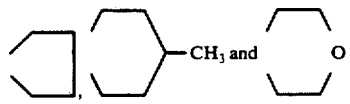

are prepared by a process comprising reacting a urea having the formula

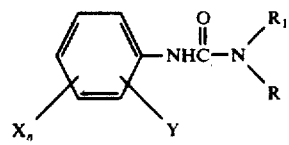

with ethyl oxalyl halide in a single step in an inert solvent.

8 Claims, No Drawings

PROCESS FOR PREPARING N-CARBAMOYL ETHYL OXANILATES

BACKGROUND AND PRIOR ART

This application relates to a novel process for the preparation of certain N-carbamoyl ethyl oxanilates. The compounds prepared by the process have the formula

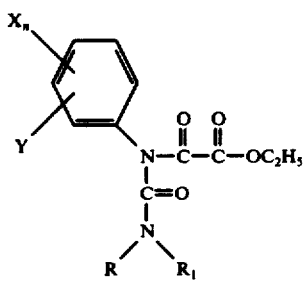

in which X and Y are independently selected from the group consisting of chloro, bromo and trifluoromethyl; n is either zero or one; and R and $R_1$ are independently selected from the group consisting of lower alkyl and lower alkoxy from $C_1$ to $C_3$ inclusive, or R and $R_1$ taken together is selected from the group consisting of

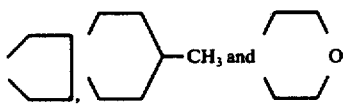

Compounds of this type, possessing utility as post and/or pre-emergence herbicides, are disclosed in the co-pending application of Edmund J. Gaughan and George B. Large titled "N-Carbamoyl Ethyl Oxanilates," Ser. No. 559,104, filed Mar. 17, 1975, now abandoned. It is disclosed therein that the compounds are prepared by reacting a 1,3,3-trisubstituted urea with sodium hydride to form a sodium salt of the urea, followed by reacting the sodium salt with ethyl oxalyl chloride to obtain the desired compound. The reactions shown in the application were all carried out using tetrahydrofuran as a solvent, and the reaction mixture was maintained under an argon blanket during at least part of the process.

It is an object of the present invention to provide a process for the preparation of N-carbamoyl ethyl oxanilates in a single step.

A further object of this invention is to provide a process for the preparation of N-carbamoyl ethyl oxanilates which can be conducted using a solvent less costly than tetrahydrofuran.

A further object of the present invention is to provide a process for the preparation of N-carbamoyl ethyl oxanilates which does not require the use of sodium hydride.

Yet another object of the present invention is to provide a process for the preparation of N-carbamoyl ethyl oxanilates which does not require maintenance of an inert atmosphere during conduct of the process.

A still further object of the present invention is to provide an improved process for the production of N-carbamoyl ethyl oxanilates of good purity and in high yield.

SUMMARY OF THE INVENTION

The invention herein comprises a process for the preparation of N-carbamoyl ethyl oxanilates having the formula

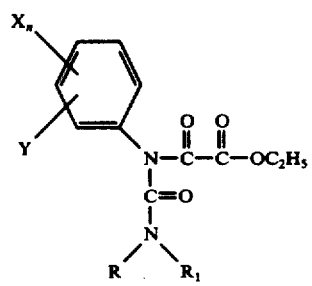

in which X and Y are independently selected from the group consisting of chloro, bromo and trifluoromethyl; n is either zero or one; and R and $R_1$ are independently selected from the group consisting of lower alkyl and lower alkoxy from $C_1$ to $C_3$ inclusive, or R and $R_1$ taken together is selected from the group consisting of

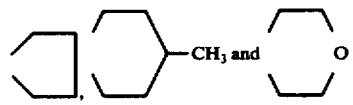

comprising reacting a urea having the formula

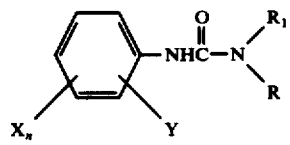

with an ethyl oxalyl halide having the formula

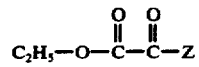

wherein Z is selected from the group consisting of chloro and bromo.

DETAILED DESCRIPTION OF THE INVENTION

The aforesaid compounds are produced in a single step by reacting a urea having the formula

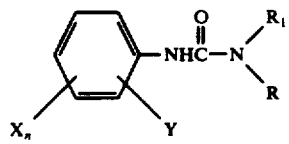

in which X, Y, n, R and $R_1$ are as previously defined with an ethyl oxalyl halide having the formula

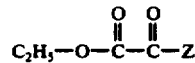

in which Z is chloro or bromo. The reaction is carried out in the presence of a solvent; however, in contrast to the process described in U.S. Pat. application Ser. No. 559,104, a less expensive solvent may be used, for example, a chlorinated hydrocarbon such as methylene chloride, chloroform, carbon tetrachloride or perchloroethylene, a hydrocarbon such as benzene or toluene, or diethyl ether. In addition, tetrahydrofuran can, if desired, be used in this reaction; however, it has been found that lower molecular weight chlorinated hydrocarbons, such as methylene chloride and chloroform are preferred.

The reaction is carried out at the boiling point of the solvent being utilized. In general, the reaction is carried out at between about 40° and about 120° C., and preferably between about 40° and about 80° C., depending on the solvent. The solvent and operating temperatures are chosen with a view toward avoiding possible thermal decomposition of the product. The reaction produces, in addition to the desired N-carbamoyl ethyl oxanilate, a hydrogen halide, i.e. either hydrogen chloride or hydrogen bromide, depending on which ethyl oxalyl halide was utilized. The pressure is maintained at about atmospheric or slightly below in order to permit removal of by-product hydrogen halide.

Examples of compounds which may be prepared by the process of the present invention are given in the following Table I.

TABLE I

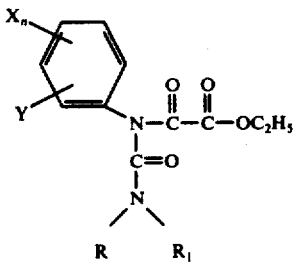

| Compound Number | X | Y | R | $R_1$ |
|---|---|---|---|---|
| 1 | — | 4-Cl | $CH_3$ | $CH_3$ |
| 2 | 3-Cl | 4-Cl | $CH_3$ | $CH_3$ |
| 3 | — | 3-$CF_3$ | $CH_3$ | $CH_3$ |
| 4 | 3-Cl | 5-Cl | ⟨pentyl ring spanning R and $R_1$⟩ | |
| 5 | 3-Cl | 4-Cl | $OCH_3$ | $CH_3$ |
| 6 | 3-Cl | 4-Br | $OCH_3$ | $CH_3$ |
| 7 | 3-Cl | 4-Cl | ⟨piperidinyl-CH_3 spanning R and $R_1$⟩ | |
| 8 | 3-Cl | 4-Cl | ⟨morpholino spanning R and $R_1$⟩ | |

The following are illustrative examples of the preparation of compounds according to the present invention:

EXAMPLE 1

Preparation of N-(dimethylcarbamoyl)ethyl-3'-trifluoromethyl oxanilate (Compound 3 of the table): A glass reactor was charged with 116 g (0.50 mole) 1,1-dimethyl-3-(3'-trifluoromethylphenyl) urea, 250 ml methylene chloride and 82 g (0.60 mole) ethyl oxalyl chloride. The resulting solution was refluxed for 7 hours at which time all the urea had been covered. The solvent and excess acid chloride were then removed by evaporation to give 161 g of a white solid, m.p. 67°–69° C., which was analyzed as 96% pure and was obtained in 97% yield.

EXAMPLE 2

Preparation of N-(dimethylcarbamoyl)-ethyl-3',4'-dichloro oxanilate (Compound 2 of the table): A 5-liter, round-bottom, four-neck flask was charged with 902 g (3.88 moles) of 1-(3,4-dichlorophenyl)-3,3-dimethyl urea and 2 liters of dry chloroform. The mixture was cooled with ice water and 610 g (4.46 moles) of ethyl oxalyl chloride were slowly added. The temperature was kept below 20° C.

After complete addition, the reaction mixture was heated at gentle reflux for 8-9 hours until the reaction was complete (the reaction was monitored by liquid phase chromatography). The solution was rotary evaporated to about one-fourth its original volume. A white solid was formed and dried, yielding 1,182 g (91% yield) of the desired compound at 98% purity (m.p. 123°–124° C.).

What is claimed is:

1. A process for the production of N-carbamoyl ethyl oxanilates having the formula

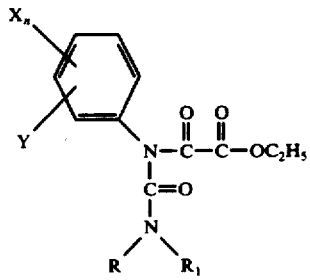

in which X and Y are independently selected from the group consisting of chloro, bromo and trifluoromethyl; $n$ is either zero or one; and R and $R_1$ are independently selected from the group consisting of lower alkyl and lower alkoxy from $C_1$ to $C_3$ inclusive, or R and $R_1$ taken together is selected from the group consisting of

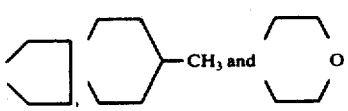

comprising reacting in an inert solvent a urea having the formula

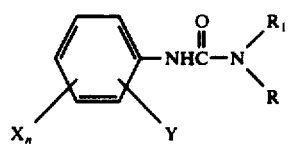

with an ethyl oxalyl halide having the formula

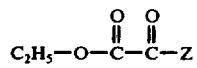

wherein Z is selected from the group consisting of chloro and bromo.

2. A process according to claim 1 conducted at a temperature of between about 40° and about 120° C.

3. A process according to claim 2 wherein the temperature is between about 40° and about 80° C.

4. A process according to claim 1 wherein Z is chloro.

5. A process according to claim 1 wherein the inert solvent is methylene chloride.

6. A process according to claim 1 wherein the inert solvent is chloroform.

7. A process according to claim 1 wherein X and Y are both chloro, $n = 1$, and R and $R_1$ are both methyl.

8. A process according to claim 1 wherein $n = 0$, Y is trifluoromethyl, and R and $R_1$ are both methyl.

* * * * *